United States Patent [19]

Mathews et al.

[11] Patent Number: 4,840,791
[45] Date of Patent: Jun. 20, 1989

[54] HAIR-WAVING PROCESS

[75] Inventors: Roger A. Mathews, Newbury Park; Edward R. Moore, Canoga Park; David W. Cannell, Los Angeles, all of Calif.

[73] Assignee: Redken Laboratories, Inc., Canoga Park, Calif.

[21] Appl. No.: 767,500

[22] Filed: Aug. 20, 1985

Related U.S. Application Data

[63] Continuation of Ser. No. 577,169, Feb. 6, 1984, abandoned.

[51] Int. Cl.$^4$ .............................................. A61K 7/09
[52] U.S. Cl. ...................................... 424/71; 132/202; 132/203; 132/204; 132/205
[58] Field of Search ................... 132/7, 202, 203, 204, 132/205; 424/71, 72

[56] References Cited

U.S. PATENT DOCUMENTS

| | | | |
|---|---|---|---|
| 2,261,094 | 10/1941 | Speakman | 132/7 |
| 2,400,377 | 5/1946 | Speakman | 424/71 |
| 3,981,312 | 9/1976 | Patel | 132/7 |
| 4,228,810 | 10/1980 | Moore et al. | 132/7 |
| 4,373,540 | 2/1983 | de la Guardia | 424/71 |
| 4,422,853 | 12/1983 | Jacquet et al. | 424/72 |
| 4,494,557 | 1/1985 | Nagel | 132/7 |

FOREIGN PATENT DOCUMENTS

| | | | |
|---|---|---|---|
| 0789521 | 7/1968 | Canada | 424/72 |
| 0799432 | 8/1958 | United Kingdom | 424/72 |

*Primary Examiner*—Shep K. Rose
*Attorney, Agent, or Firm*—Christie, Parker & Hale

[57] ABSTRACT

A process for the permanent waving of hair in which hair wound on a mandrel is exposed to the action of a reactive waving solution containing at least one reducing agent capable of cystine cleavage to achieve cystine cleavage and the step of applying an oxidizing agent to the hair to reform the cystine bonds, is improved by contacting the hair for from about 5 to 15 minutes with the reactive waving solution to achieve a substantially-maximum cystine bond cleavage; blotting the hair to remove the reactive waving solution; and contacting the hair with a protein flow solution for a period of time sufficient to induce protein flow in the hair to achieve a desired curl configuration prior to application of the oxidizing agent to reestablish the cystine bonds to fix the curl. The protein flow solution is an aqueous protein flow solution having a pH of from about 2 to about 10. The protein flow solution is preferably an aqueous solution of at least one protein flow agent which is a polyvalent metal ion, a water-soluble hydroxyorganic compound containing up to about 4 carbon atoms, and at least one hydroxyl group or mixtures thereof.

2 Claims, 3 Drawing Sheets

HAIR-WAVING PROCESS

This is a continuation of application Ser. No. 577,169, filed Feb. 6, 1984, now abandoned.

BACKGROUND OF THE INVENTION

In the process of permanent-waving, or "perming", of hair, the overall sequence may be expressed as follows:

1. Penetration of a reducing agent into hair
2. $kSSk + RSH \rightleftharpoons kSH + RSSk$
3. $kSSR + RSH \rightleftharpoons kSH + RSSR$
4. Rearrangement of protein chains.
5. Setting the curl by reforming cystine bonds.

It has been reported in the literature that under alkaline waving conditions, penetration is the slow step, with steps 2 and 3 presumably taking place as rapidly as penetration occurs. The fourth step is critical to the formation of a commercially acceptable curl. Under acid conditions, e.g., pH 5 to 7, it has been considered necessary to apply heat to achieve a proper curl. This is because step 2 is the dominant or limiting step. Under such conditions, the hair is highly susceptible to reformation of cystine bonds on rinsing through reversal of reaction 2.

Under alkaline conditions, the reaction proceeds well through step 3, with increased formation of cysteine (kSH) and concomitant loss of mixed disulfide (kSSR). It is for this reason that alkaline waving solutions have been favored by the beauty industry.

In conventional perming, therefore, the hair is contacted, after washing, with a waving solution of a reducing agent, normally a mercaptan, present in sufficient strength to cleave the cystine (disulfide) bond. Cleavage softens the protein structure (keratin) of the hair. Contact time depends on pH, the process used, and temperatures employed, which may be up to about 60° C. Wetting agents or other penetrants are normally employed to aid reduction.

In practice, the key objective is to complete the waving process in less than one hour, with the safety and comfort of the client foremost in mind. Hair that has been chemically pretreated may be contacted with weaker solutions and for a lesser time than normal hair. Solutions of high reductant concentration may be required for hair difficult to treat, or to shorten process time.

The operator normally determines whether there has been adequate processing of the hair, or that maximum bond breakage has occurred, by formation of a test curl. This determination involves unrolling the mandrel a couple of curls to ascertain if a "soft S" at the diameter of the mandrel pattern has formed. This is a subjective but skilled determination of whether adequate softening of the hair has occurred, so as to produce a satisfactory wave, and is normally expressed by the operator as the time of contact of the waving solution with the hair. When adequate test curl has been achieved, the waving solution is normally rinsed from the hair, and while the hair is still set on mandrels, an oxidizing agent is applied to fix the new curl pattern. The hair is subjected to a final rinse, possibly with conditioning, then dried.

SUMMARY OF THE INVENTION

The present invention is directed to achieving permanent waves by a precise sequence of steps which reduce the potential of damage to the hair or scalp, shorten the overall waving cycle, and insure a better curl.

In its broadest aspects, the invention resides in exposing hair wound on a mandrel to the action of a reactive waving solution containing at least one reducing agent capable of cystine cleavage, for a time sufficient to achieve substantially maximum bond cleavage; followed by blotting the hair to remove excess waving solution; then applying a suitable protein flow solution to enable protein flow to the desired curl configuration (reaction 4). This is followed by oxidation using an oxidizing agent to reestablish the cystine bonds to fix the curl.

Preferably, the method involves contacting the conditioned hair with a waving solution comprised of at least one water-soluble mercaptan capable of cleaving the cystine bonds, and preferably present in combination with an alkali to maintain pH at from about 6 to about 10, and present in a concentration sufficient to achieve maximum bond-cleavage in from 5 to 15 minutes, contemporaneously with penetration of the hair; blotting excess waving solution from the hair; then contacting the hair with a suitable protein flow solution, preferably comprising an aqueous solution of at least one polyvalent ion and/or a hydroxyorganic compound containing one or more hydroxyl groups and up to about 4 carbon atoms at a pH of from 2 to about 10, for a period of from about 5 to about 10 minutes. This is followed by rinsing and reforming the cystine bonds through oxidation with a conventional peroxide or bromate oxidizing solution.

THE DRAWINGS

FIGS. 1–3 graphically illustrate the degree of reduction of cystine (S-S), shown by "."; cysteine (S-H) formation is shown by "O"; and the mixed disulfides (CMTC) are shown by "X".

FIG. 1, in particular, is the plot of the kinetic change in hair as a function of time, using as the reducing agent an alkaline solution containing 7% by weight ammonium thioglycolate (ATG) at a pH of 9.5, which solution contains about 5% by weight nonionic surfactants.

Figure 6:
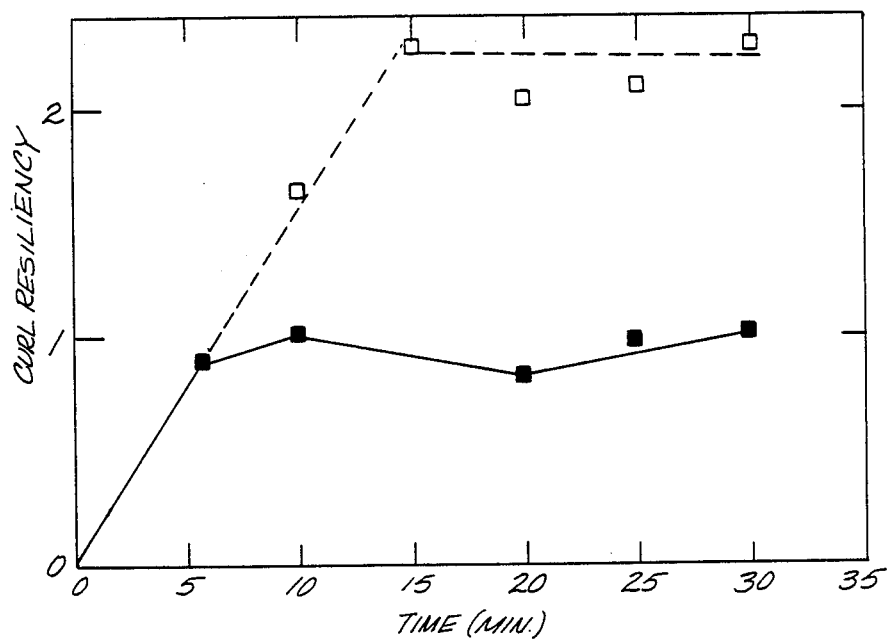

FIG. 6 illustrates the dramatic difference in waving using the same waving solution by practice of the instant invention. Blotting occured at a 5-minute interval. The points after blot show resiliency at points in time after rinsing of the hair and rebonding. The solid line represents a plot for curl resiliency against time using as the waving solution, Redken CLIMATRESS ®, an alkaline ammonium thioglycolate solution, in a conventional waving process. The dashed line shows resiliency produced by using an aqueous protein flow solution of magnesium sulfate and ethanol.

DETAILED DESCRIPTION

The instant invention will be detailed by a comparison of results achieved in conventional waving and the differences realized by practice of the instant invention.

As used herein, the term "maximum bond cleavage" is defined as the maximum fraction of cystine (disulfide) bonds cleaved during the waving process, as determined by analysis of cysteine content with time. Normally, at least 30% cleavage of cystine is required, and from about 30% to about 50% is normally obtained in a successful wave.

"Test curl" is the visual determination of softening to produce a satisfactory wave by one skilled in perming. It is expressed as the time of contact with the waving solution.

"Efficiency" is the measure of appearance of curl tightness by waving hair on mandrels (pegs) of predetermined spacing. It is expressed as the percentage of maximum tightness, as determined by the geometry of spacing. High efficiencies represent tight-curl appearance but not necessarily resiliency.

"Resiliency" is the measure of regain of curl or spring, as determined by extending or stressing the curl pattern waved on pegs of predetermined spacing. The tighter the return, or regain, the more resilient the curl formed. A curl may be tight in appearance, but not resilient. The converse is also true.

"Mature curl" is the curl pattern that is found at the time of test curl, and is expressed as a resiliency value that is commercially acceptable, compared to resiliency of accepted perm products.

"Protein flow" is the molecular rearrangement of the keratin-protein chains to form the curl pattern for the mature curl. In contrast to popular view, "protein flow" is not synonymous with "cystine cleavage".

By "hydroxyorganic compound" there is meant an alcohol or a polyvol containing up to about 4 carbon atoms.

By "polyvalent ion" there is meant an ion, when in solution, having a valence of at least 2. Cations are preferably present. However, anions have also been observed to be functional.

Cystine cleavage is, in accordance with this invention, an operation independent of induced protein flow. As separate operations, more efficient permanent waves are achieved in shorter time spans with less client discomfort.

The nature of the perming operation is to first shampoo the hair, then to wind the hair on mandrels. There is then applied to the hair a waving solution of at least one reductant for cystine (S-S) bonds, which may be from acid to alkaline in nature. Suitable reductants include thioglycolic acid; thiolactic acid; cysteine; salts and derivatives thereof; sulfite salts and the like. With reference to the background of the invention, alkaline, as opposed to acid, waving solutions are preferably used. This is because the acid waving solution is more-or-less limited, independent of waving solution concentration and application of heat, to the reaction of step 2, whereas steps 3 and 4 readily occur in an alkaline system having a pH greater than 7. Moreover, under acid conditions, fiber swelling is at a minimum, an ionic attractions between protein side-chains are at their maximum.

It is for these reasons, in part, that thioglycolicacid and similar solutions at a pH between 5 and 7 are less preferred than waving solutions of the same agent at an alkaline pH.

Under preferred alkaline conditions, the reaction, as indicated, proceeds well through step 3, with increased formation of cysteine (kSH) and concomitant loss of mixed-disulfide (kSSR) bonds. In addition, the protein chains bear an excess of negative charges, increasing hair swelling, which induces protein flow through repulsion. In consequence, the initial concentration of mixed disulfides is rapidly consumed, and the process normally proceeds through step 4 with attendant protein flow as determined by the skilled permer to have occurred, as a measure that a mature curl can be formed.

It has now been found that substantially-maximum cystine cleavage (step 2) can be achieved using any conventional, reactive waving solution for about 5 minutes, with any excess time being created by reagent concentration, pH, temperature or hair condition. Normally, the maximum time is about 10 minutes, and cleavage is synchronous with penetration. Any time longer than about 15 minutes is unnecessary to the invention. This is because, in the practice of the instant invention, a secondary, less noxious means is used to induce protein flow, namely, the use of a protein flow solution as defined herein.

As is conventional, cleavage for an acid waving solution proceeds through steps 1 and 2; and for an alkaline waving solution, cleavage proceeds to or into step 4. Independent of pH, the hair is blotted to remove excess waving solution, to maintain equilibrium of established cystine cleavage. Rinsing at this point is avoided because of reversal of step 2 to form cystine. Rather, protein flow is induced with a protein flow solution. Preferably, the protein flow solution employed is an aqueous solution of a water-soluble hydroxyorganic compound and/or a polyvalent ion, as detailed below.

If the waving solution is based on glycerol monothioglycolate under generally neutral conditions, protein flow solutions described herein may be employed, since glycerol monothioglycolate is intermediate, and by the fact that it is more ionized under acid conditions, with a $pK_{SH}$ of 7.8 relative to a $pK_{SH}$ of 10.2 for thioglycolic acid.

It is preferred, however, to employ a solution comprising at least one alcohol and/or polyol in combination with at least one polyvalent ion.

Disrupting agents, such as urea, quanidine, amides, betaines and surfactants which aid in expanding the protein structure, may be included in the protein flow solutions employed.

For practice of the instant invention, therefore, after treating the hair with the waving solution for a period of from about 5 to about 15 minutes, excess waving solution is blotted from the hair. This leaves the remainder in the fiber to maintain maximum bond cleavage for subsequent protein rearrangement with a protein flow solution.

Protein rearrangement is then achieved by applying to the hair, an aqueous protein flow solution comprising at least one water-soluble salt of a polyvalent ion having an ionic charge of at least two, and acceptable toxicity. Magnesium and calcium salts are currently preferred. Salts may be used in concentrations up to solution saturation, normally in a concentration of from about 1 to about 10 percent by weight. Alternatively, but preferably in addition, there is employed at least one hydroxyorganic compound containing up to about 4 carbon atoms. It may be an alcohol and/or a polyol. Again, concentration may be up to solution saturation or to a concentration where the solution becomes hazardous to the client or to use. Illustrative but not limiting of functional compounds, there may be mentioned, ethanol, isopropanol, butanol, isoamyl alcohol, propylene glycol and the like. Normally, 2-butanol is not used because of odor. Methanol is functional, but can present toxicity problems. Normally, the alcohol or the polyol is present in a concentration up to about 25 percent by weight of solution, preferably from about 1 to about 20 percent by weight, more preferably from about 2 to about 10 percent by weight. Solution pH may range from about 2 to about 10, preferably from about 6 to about 7, and may be adjusted by inclusion of alkaline compounds such as ammonia, alkaline amino acids, alkanolamines, alkali carbonates, and the like.

Preferably, there are contained in the protein flow solution, wetting agents, such as nonionic, cationic or anionic detergents; conditioners, such as amino acids or proteins; polymers or water-soluble fatty derivatives, as thickeners; colorants; fragrance; preservatives, and the like.

While not bound by theory, it is believed that the application of the ionic solution produces a concentration gradient, inducing the fibers to absorb positively-charged ions which neutralize negatively-charged protein side chains, causing increased protein mobility and inducing flow.

The alcohol or polyol ingredient induces penetration and hydrophobic rearrangement of protein side chains further increasing thereby the propensity to flow. Protein flow is complete within a period of from 5 to 10 minutes, which is predetermined by the precise composition, temperature, and condition of the hair.

In the practice of the instant invention, although two applications of solution are employed, the waving operation is faster, having a feasible maximum completion time of 15 minutes, with more repeatable and reliable results for the cleavage and rearrangement steps.

Following addition of the protein flow solution to the hair, the hair is rinsed and the disulfide bonds are reformed through conventional oxidizing operations, as by application of peroxide and bromate rebonding solutions.

The following are preferred acid and alkaline systems for use in the present invention.

ACID

| Reformer Glycerol Monothioglycolate | |
|---|---|
| Balancer | (% by weight) |
| Ammonia | 0.34% to 0.85% |
| Urea | 1.00% to 15.00% |
| Nonionic Surfactant | 1.00% to 6.00% |
| Fragrance | 0.10% to 0.50% |
| Water | Balance |

The Reformer and the Balancer are combined at time of use in proportions to provide a pH of from 6.8 to 7.0.

| | (% by weight) |
|---|---|
| Flow Solution | |
| Nonionic Surfactant | 0.50% to 6.00% |
| Fragrance | 0.10% to 0.50% |
| Absolute Alcohol | 2.00% to 5.00% |
| Magnesium Sulfate | 1.00% to 15.00% |
| Water | Balance |
| Bonding Lotion | |
| Nonionic Surfactant | 1.00% to 5.00% |
| Fragrance | 0.10% to 0.50% |
| $H_2O_2$ (50%) | 3.00% to 5.00% |
| Water | Balance |

ALKALINE

| | (% by weight) |
|---|---|
| Reforming Lotion | |
| Ethylenediamine-tetracetic acid | 0.5% |
| Nonionic Surfactant | 2.00% to 6.00% |
| Urea | 1.00% to 15.00% |
| Fragrance | 0.5% |
| Ammonium Thioglycolate | 8.00% to 12.00% |
| Aqua Ammonia (28%) | 2.12% to 5.00% |
| Water | Balance |
| pH | 9 to 9.5 |
| Flow Lotion | |
| Nonionic Surfactant | 0.50% to 6.00% |
| Fragrance | 0.10% to 0.50% |
| Absolute Alcohol | 2.00% to 5.00% |
| Magnesium Sulfate | 1.00% to 15.00% |
| Water | Balance |
| Bonding Lotion | |
| Nonionic Surfactant | 1.00% to 5.00% |
| Fragrance | 0.10% to 0.50% |
| $H_2O_2$ (50%) | 3.00% to 5.00% |
| Water | Balance |

Examples and Controls

EXAMPLE 1

A series of studies were conducted to ascertain the degree of cystine cleavage achieved within 5 minutes. Table I shows typical cleavage for alkaline and acid (ammonium thioglycolate) and neutral (glycerol monothioglycolate) waving solutions. The hair was from the same subject. In each case the reducing agent was present at a concentration of 7% by weight.

TABLE I

| Wave Type | Typical Cystine Cleavage - 5 Min. |
|---|---|
| Alkaline (pH 9.2) | 56% |
| Acid (pH 6.8) | 36% |
| GMTG (pH 7.0) | 33% |

Figure 1:
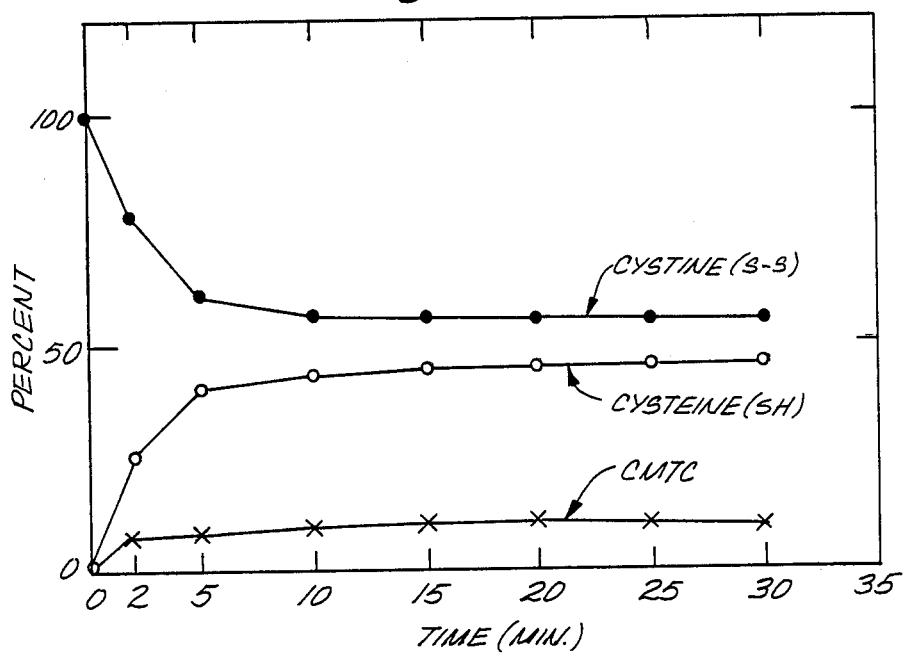
Figure 2:
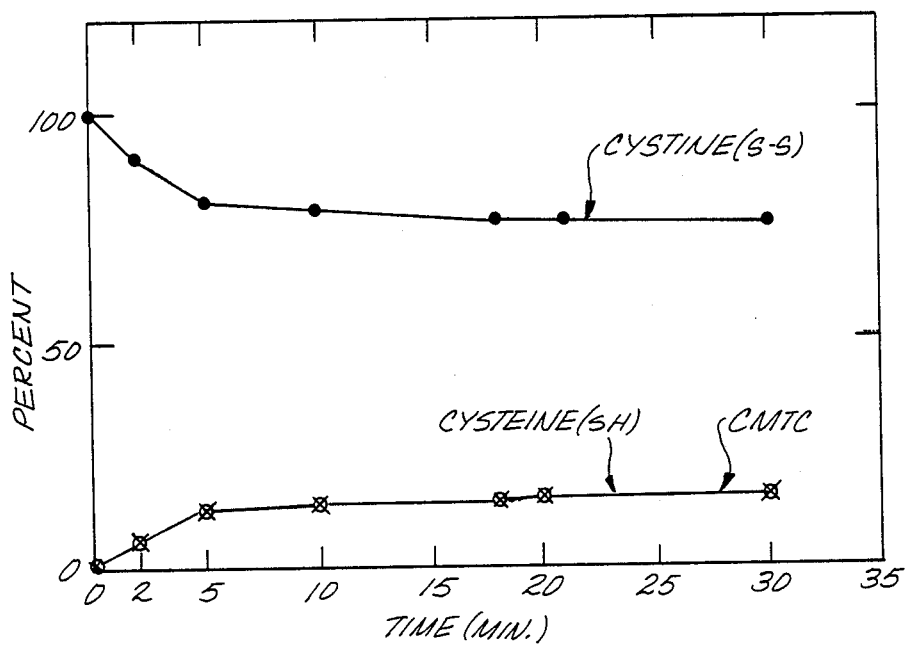
FIG. 2 illustrates the kinetics of acid hair-reduction, using a 7%-by-weight ammonium thioglycolate waving solution at a pH of 6.9 and containing 5% by weight nonionics. It will be noted that the cysteine and CMTC curves coincide.
Figure 3:
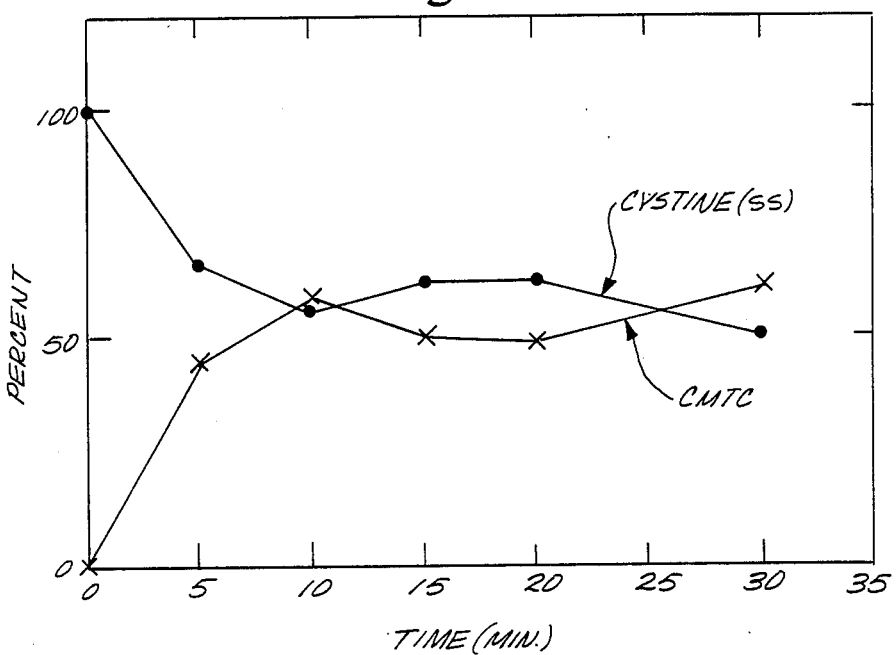
FIG. 3 illustrates the kinetics of hair-reduction, using glycerol monothioglycolate (GMTC), also under acid conditions.

FIG. 1 shows kinetics of performance of an alkaline waving solution (7% by weight ammonium thioglycolate plus 5% by weight nonionics at pH 9.5), while FIGS. 2 and 3, respectively, show the kinetics of cystine cleavage for acid waving solutions (7% by weight ammonium thioglycolate plus 5% by weight nonionics at pH 6.9) and CREATIVE CURL ®, a commercial acid waving solution containing 14.7% by weight glycerol monothioglycolate (GMTG). All establish that maximum or substantially maximum bond cleavage occurred in 5 minutes with, in the instance of GMTG, some gain in the 5-to-10-minute span. It was concluded, therefore, that in most instances, substantially maximum bond cleavage could be achieved in from 5 to 10 minutes.

Control A

In a controlled salon test, cystine and CMTC content of a controlled amount of hair were determined at various points in a waving operation. It established that the amount of cystine did not decrease, nor did mixed disulfides increase, with protracted contact with the waving solution. It also showed the strong influence of water on restoring the cystine bonds. The waving solution was composed of 11% by weight ammonium thioglycolate, a nonionic surfactant, at a pH of 7.0.

TABLE II

|  | Weight % | | | |
| --- | --- | --- | --- | --- |
| Step | Cystine | | CMTC | |
| Shampoo | 14.9 | 0.1 | Trace | |
| 5 Min. after Application of Waving Solution | 5.4 | 0.0 | 6.2 | 0.1 |
| 25 Min. after Application of Waving Solution | 5.6 | 1.0 | 5.0 | 0.1 |
| Rinse (H$_2$O) | 11.0 | 0.1 | 1.4 | 0.3 |
| Oxidation | 13.1 | 0.1 | 1.9 | 0.0 |

EXAMPLE 2

To further confirm that effective cleavage was achieved in 5 minutes, 12 clients were subjected to an acid wave (11% by weight ATG, pH 6.9, at 50° C.) and an alkaline wave (7% by weight ATG, pH 9.2, at room temperature), respectively, with a water rinse to restore cystine. The results are shown in Tables III and IV.

TABLE III

|  | Acid Wave |
| --- | --- |
| Parameter | Average |
| % Cleavage Cystine | 48% ± 5% |
| % Restoration Cystine by Water Rinse | 59% ± 30% |
| % Restoration Cystine by Oxidizer | 86% ± 7% |

TABLE IV

|  | Alkaline Wave | |
| --- | --- | --- |
| Parameter | Average | Range* |
| % Cleavage Cystine | 29% ± 7% | 20% to 43% |
| % Restoration Cystine by Water Rinse | 69% ± 22% | 38% to 135% |
| % Restoration Cystine by Oxidizer | 95% ± 6% | 78% to 113% |

*values greater than 100% due to available bonding sites being linked by water or oxidizer to form additional cystine bonds

EXAMPLE 3

The following Table V shows curl resiliency as a function of the composition of the protein flow solution applied after blotting. Blotting was preceded by a 5-minute wave using a 7%-by-weight solution of ammonium thioglycolate at pH 9.2.

TABLE V

|  | Curl Resiliency | |
| --- | --- | --- |
| Step 2 | At 0 mg Stress | At 10 mg Stress |
| Water Only | 1.8 | 1.1 |
| 5% by Weight MgSO$_4$(a) | 2.7 | 1.7 |
| 5% by Weight SDA-40(a) | 2.3 | 1.4 |
| 5% by Weight MgSO$_4$(a) + 5% by Weight SDA-40(a) | 2.9 | 1.9 |

(a)balance water SDA-40 is denatured, absolute ethanol

EXAMPLES 4 AND 5

Figure 4:
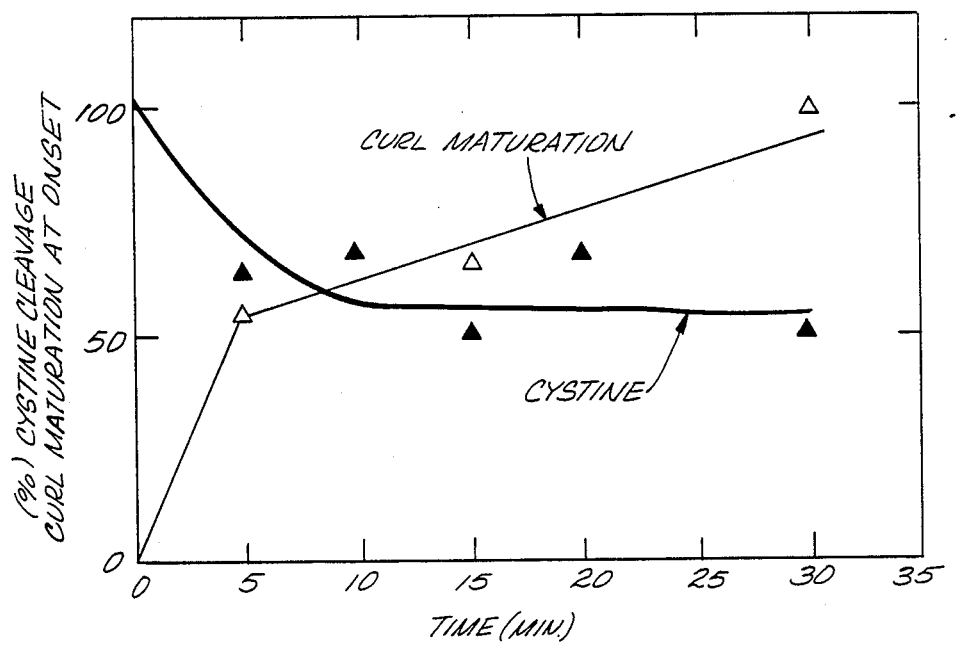
FIGS. 4 and 5 illustrate, respectively, curl maturation at onset and curl efficiency vs. cleavage as a function of time, which establishes maturation lags cleavage of cystine.
Figure 5:
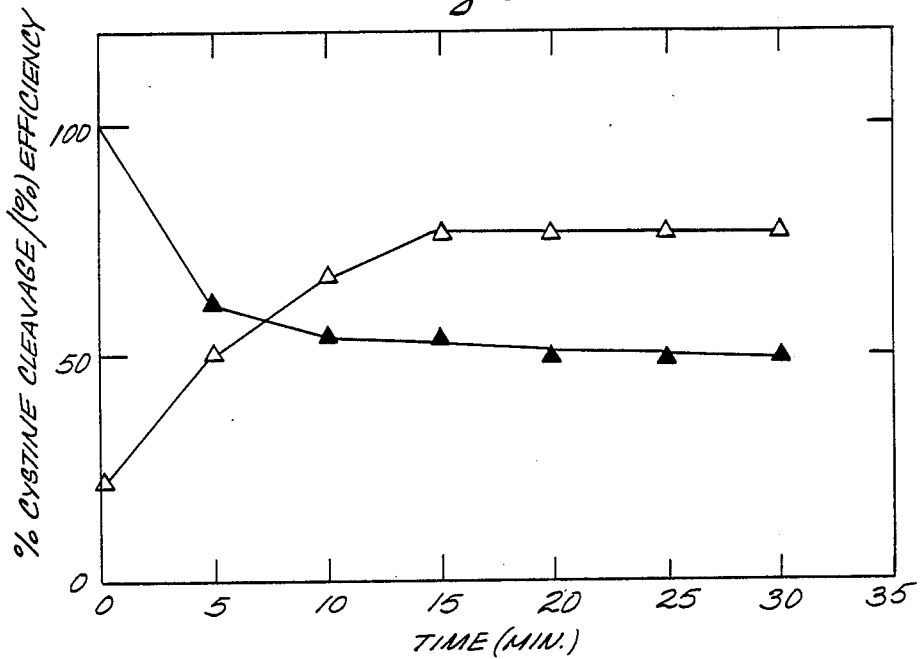

Tests were conducted with respect to curl maturation at onset versus cleavage. FIG. 4 shows curl maturation at onset, and FIG. 5 shows curl maturation as a percentage of efficiency, versus cysteine cleavage. It was determined, unlike the prior art, that maturation was delayed relative to cleavage, with protein flow being the limiting step. This enabled the protein flow to be treated as a factor independent of cleavage. The waving solution used for the tests was composed of 7% by weight ammonium thioglycolate and 5% by weight nonionic surfactant at a pH of 7.0 at 50° C.

EXAMPLE 6 AND CONTROLS B AND C

Table VI shows the results of using the same waving conditions, namely, 5-minute contact with a 7%-by-weight ATG solution at pH 9.2, but where the variants were blotting and the solution applied.

TABLE VI

| Control or Example | Composition | | | Percent Efficiency Test Curl | Curl Resiliency | |
| --- | --- | --- | --- | --- | --- | --- |
|  | Step 1 | Blot/ Rinse | Step 2 |  | at 0 mg Stress | at 10 mg Stress |
| Con. B | 5 Min. 7% ATG pH 9.2 | Blot | 10 Min. Water | 64% | 1.4 | 1.0 |
| Ex. 6 | 5 Min. 7% ATG pH 9.2 | Blot | 10 Min. 5% MgSO$_4$* 5% Isopropanol* | 74% | 3.0 | 2.1 |
| Con. C | 5 Min. 7% ATG pH 9.2 | Rinse | 10 Min. Polyamide-Epichlorohydrin Solution(b) | 52% | 1.6 | 1.0 |

(b) See U.S. Pat. No. 3,981,312.
*% by weight

FIG. 6 dramatically shows the effect of using the instant invention. Curl resiliency with water rinse did not improve by delaying water addition for shown periods of time after blotting, whereas application of the protein flow solution for 10 minutes after blotting increased resiliency by 100%.

EXAMPLE 7

The following Table VII shows the performance of various alcohols and glycols (at 5% by weight) in supplementing 5% MgSO$_4$ in a protein flow solution. The solution was applied after blotting hair which had been contacted by a 7%-by-weight ATG solution at a pH of 9.2 for 5 minutes. Contact time with the protein flow solution was 10 minutes.

TABLE VII

| 5% by Weight MgSO$_4$ Plus . . . | Curl Resiliency | |
| --- | --- | --- |
|  | At 0 mg Stress | At 10 mg Stress |
| 5% by Weight SDA-40 | 2.6 | 1.6 |
| 5% by Weight Isopropyl Alcohol | 2.9 | 1.7 |
| 5% by Weight | 2.4 | 1.6 |

TABLE VII-continued

| 5% by Weight MgSO4 Plus... | Curl Resiliency | |
|---|---|---|
| | At 0 mg Stress | At 10 mg Stress |
| Propylene Glycol | 3.0 | 1.9 |
| 5% by Weight 2-Butanol | 2.5 | 1.7 |
| 5% by Weight 1-Butanol | 2.7 | 1.8 |
| 5% by Weight tert-Butanol | 3.0 | 1.9 |
| 5% by Weight Methanol | 2.4 | 1.4 |
| 5% by Weight IsoAmyl Alcohol | | |

What is claimed is:

1. In a process for the permanent waving of hair in which, washed hair wound on a mandrel is subjected to the action of a reactive waving solution applied to the mandrel-wound hair, the waving solution having a pH of from 6.8 to 7.0 containing, for cleavage of the cystine bonds, glycerol monothioglycolate and the step of applying peroxide oxidizing agent to the mandrel-wound hair, after rinsing of the hair, to reform the cystine bonds, the improvement which comprises:
   (a) blotting the hair after cleavage of the cystine bonds to remove reactive waving solution from the hair leaving a remainder to maintain the level of cleaved cystine bonds;
   (b) applying to the blotted mandrel-wound hair a protein-flow solution and allowing the protein-flow solution to remain in contact with the hair for a period of time of from about 5 to about 10 minutes to induce protein flow in the hair to achieve a desired curl configuration, said protein-flow solution being an aqueous protein-flow solution having a pH from about 2 to about 10 and said protein-flow solution being an aqueous solution of magnesium sulfate present in concentration of about 1 to 10 percent by weight of solution of, and a water-soluble hydroxyorganic compound containing up to about 4 carbon atoms and at least one hydroxyl group present in a concentration of from 2 percent by weight up to 5 percent by weight of solution, and 0.5 to 6 percent by weight nonionic surfactant and thereafter;
   (c) rinsing the protein-flow solution from the mandrel-wound hair; and
   (d) applying the oxidizing agent to the mandrel-wound hair to reestablish the cystine bonds to fix the curl.

2. A process for the permanent waving of hair which comprises:
   (a) winding washed hair on a mandrel
   (b) applying to a reactive waving solution containing glycerol monothioglycolate in combination with a balancing solution comprising from 0.34 to 0.85 percent by weight ammonia and 1.00 to 15.00 percent by weight urea and 1.00 to 6.00 percent by weight nonionic surfactant and having a pH of from 6.8 to 7 for a time of from 5 to 15 minutes to achieve cystine bond cleavage;
   (c) blotting the mandrel-wound hair to remove reactive waving solution from the hair leaving a remainder of the reactive waving solution in the hair to maintain cystine bond cleavage; then
   (d) applying to the hair containing reactive waving solution remaining after blotting, a protein-flow solution and allowing the applied protein-flow solution to contact the hair for a period of from about 5 to about 10 minutes to induce protein flow in the hair to achieve a desired curl configuration, said protein-flow solution being an aqueous solution having a pH from about 2 to about 10 and containing magnesium sulfate present in a concentration of from about 1 to about 10 percent by weight, and ethyl alcohol present in a concentration of from about 2 to about 5 percent by weight of solution and a nonionic surfactant present in a concentration of from 0.50 to 6.00 percent by weight of solution and thereafter;
   (e) rinsing the protein-flow solution from the hair and closing the cystine bonds by application of an aqueous oxidizing agent containing 3.00 to 5.00 percent by weight of a 50 percent hydrogen peroxide solution.

* * * * *